United States Patent
Nam et al.

(10) Patent No.: US 10,533,206 B2
(45) Date of Patent: Jan. 14, 2020

(54) METHOD FOR SELECTIVELY PRODUCING COMPOUND K AND COMPOUND Y FROM SAPONINS OF GINSENG THROUGH ENZYMATIC METHOD

(71) Applicant: AMOREPACIFIC CORPORATION, Seoul (KR)

(72) Inventors: Gi Baeg Nam, Yongin-si (KR); Dong Hyun Kim, Yongin-si (KR); Yong Deog Hong, Yongin-si (KR); Cheng Yi Zhang, Yongin-si (KR); Jun Seong Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/770,019

(22) PCT Filed: Oct. 21, 2016

(86) PCT No.: PCT/KR2016/011910
§ 371 (c)(1),
(2) Date: Apr. 20, 2018

(87) PCT Pub. No.: WO2017/069569
PCT Pub. Date: Apr. 27, 2017

(65) Prior Publication Data
US 2018/0312894 A1 Nov. 1, 2018

(30) Foreign Application Priority Data
Oct. 22, 2015 (KR) .................. 10-2015-0147355

(51) Int. Cl.
| | |
|---|---|
| *C12P 33/16* | (2006.01) |
| *C12P 19/44* | (2006.01) |
| *C07H 17/00* | (2006.01) |
| *C07J 17/00* | (2006.01) |
| *C12N 9/24* | (2006.01) |
| *C12N 9/42* | (2006.01) |
| *C12P 33/20* | (2006.01) |

(52) U.S. Cl.
CPC .............. *C12P 33/16* (2013.01); *C07H 17/00* (2013.01); *C07J 17/00* (2013.01); *C12N 9/24* (2013.01); *C12N 9/2437* (2013.01); *C12P 19/44* (2013.01); *C12P 33/20* (2013.01); *C12Y 302/0104* (2013.01); *C12Y 302/01004* (2013.01); *C12Y 302/01015* (2013.01)

(58) Field of Classification Search
None
See application file for complete search history.

(56) References Cited

FOREIGN PATENT DOCUMENTS

| KR | 10-2008-0028266 A | 3/2008 |
| KR | 10-2010-0107865 A | 10/2010 |
| KR | 10-2013-0105174 A | 9/2013 |
| KR | 10-2015-0030012 A | 3/2015 |

OTHER PUBLICATIONS

Lee et al. Process Biochem. (2012) 47: 538-543 (Year: 2012).*
Sung-Ryong Ko, et al., "Marked Production of Ginsenosides Rd, $F_2$, $Rg_3$, and Compound K by Enzymatic Method[1]", Chemical and Pharmaceutical Bulletin, 2007, pp. 1522-1527, vol. 55, No. 10.
Fei Gao, et al., "Biotransformation, a Promising Technology for Anti-cancer Drug Development", Asian Pacific Journal of Cancer Prevention, 2013, pp. 5599-5608, vol. 14, No. 10.
International Search Report for PCT/KR2016/011910 dated Feb. 15, 2017 [PCT/ISA/210].

* cited by examiner

*Primary Examiner* — Susan M Hanley
(74) *Attorney, Agent, or Firm* — Sughrue Mion, PLLC

(57) ABSTRACT

The present invention relates to a method for selectively producing compound K and compound Y, which are originally present in ginseng in a trace amount, from saponins of ginseng, and more specifically to a method capable of obtaining desired target compounds, that is, compound K and compound Y, in high yields, by treating saponins, obtained from ginseng, with particular enzymes to structurally convert the saponins.

7 Claims, 1 Drawing Sheet

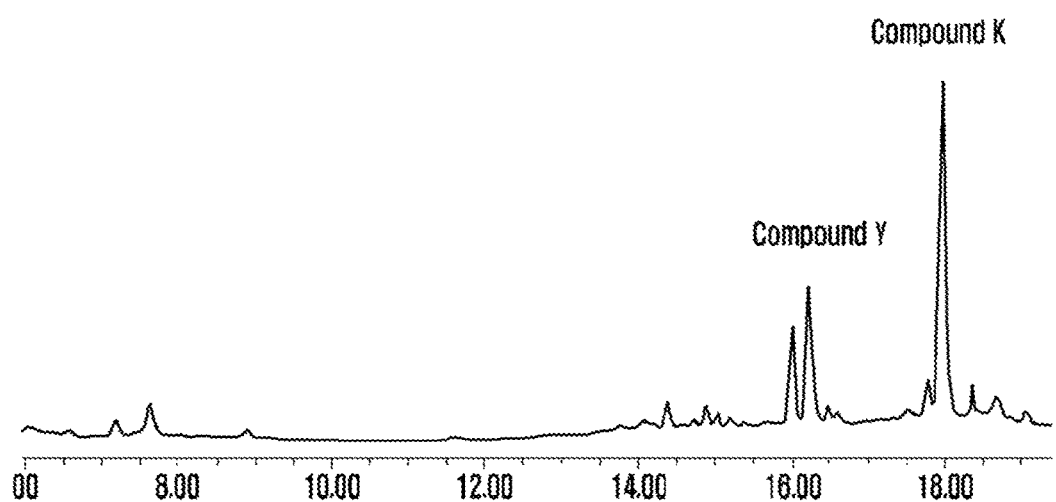

METHOD FOR SELECTIVELY PRODUCING COMPOUND K AND COMPOUND Y FROM SAPONINS OF GINSENG THROUGH ENZYMATIC METHOD

CROSS REFERENCE TO RELATED APPLICATIONS

This application is a National Stage of International Application No. PCT/KR2016/011910, filed on Oct. 21, 2016, which claims priority from Korean Patent Application No. 10-2015-0147355, filed on Oct. 22, 2015.

TECHNICAL FIELD

The present invention relates to a method for selectively producing compound K and compound Y, which are originally present in ginseng in a trace amount, from saponins of ginseng, and more specifically to a method capable of obtaining desired target compounds, that is, compound K and compound Y, in high yields, by treating saponins, obtained from ginseng, with particular enzymes to structurally convert the saponins.

BACKGROUND ART

*Ginseng* saponin has a unique chemical structure different from that of saponin found in other plants. Thus, its pharmacological efficacy is unique, and thus it is also called "ginsenoside" in the sense of ginseng glycoside. Specific types of ginseng saponins include panaxadiol-type ginsenosides Rb1, Rb2, Rc, Rd, compound K, compound Mc, compound O, etc., and panaxatriol-type ginsenosides Re, Rf, Rg1, Rg3, Rg5, Rh1, Rh2, etc., and each of these ginseng saponins exhibit different efficacies.

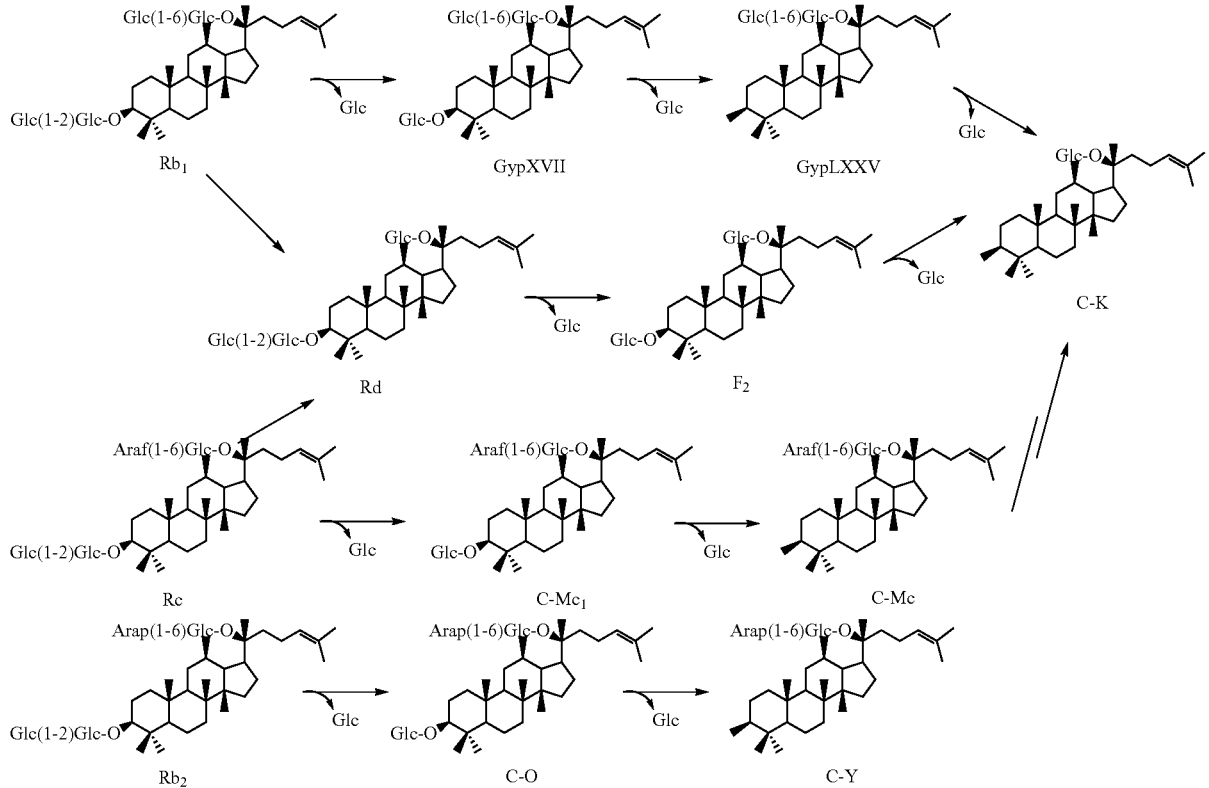

[Reaction Scheme 1]

As shown in the Reaction Scheme 1, particularly, since ginsenosides Rb1, Rb2, Rc, etc., which are panaxadiol type saponins, can be converted into other ginseng saponins by metabolism of microorganisms, a method using enzymes has been used for a long time as a method of converting ginseng saponin into other kinds of specific ginseng saponins.

However, for the conversion reaction using enzymes in the past, non-specificity of enzymes for a substrate is large and thus an extremely large amount of enzyme should be used relative to the saponin substrate used. Further, the enzymatic reaction is not completed with a desired ginseng saponin, but an additional reaction occurs nonspecifically. Thus, since other ginseng saponins were variously produced without being converted only to the desired ginseng saponin, the yield of the desired ginseng saponin was extremely low.

Conventional methods of obtaining ginseng saponins do not convert only to a desired specific ginseng saponin, but provide a technical solution of obtaining various converted ginseng saponins by extraction or the like and then purifying the resultant to isolate only desired ginseng saponins.

However, since these conventional methods require additional cost and time associated with the purification in order to obtain a pure specific ginseng saponin. Therefore, the selling price of ginseng saponins is inevitably increased, and there is a limit to applying a large amount of ginseng saponins to related products.

In particular, in the case of compound K, it corresponds to the compound which is finally produced in the pathway of the compound converted from ginseng saponin, and thus a variety of enzymes capable of reacting all intermediate metabolites are required, and further, the reactivity between the metabolite and the enzyme decreases due to metabolic products generated during the reaction. In addition, a problem arises that the yield decreases due to aggregation phenomena in the reaction solution between intermediate metabolites.

PRIOR ART LITERATURE

Patent Literature

1. Korean Patent Laid-Open Publication No. 10-2010-0107865 (published on Oct. 6, 2010)

DETAILED DESCRIPTION OF THE INVENTION

Technical Problem

It was expensive to acquire a specific ginseng saponin by a conventional method and also it was difficult to obtain the desired ginseng saponin in large quantities. Therefore, there is a need to develop a production method that can produce a large amount of target ginseng saponins and can save costs.

Accordingly, an object of the present invention is to provide a conversion method of ginseng saponin which can obtain a desired specific ginseng saponin in a high yield and also can be easily carried out Technical Solution In order to achieve the above object, the present invention provides a method for producing compound K and compound Y in a high yield by converting saponins of ginseng using at least one selected from the group consisting of pectinase, naringinase, cellulase and hemicellulase isolated from a microorganism of the genus *Aspergillus*; and at least one selected from the group consisting of pectinase and cellulase isolated from a microorganism of the genus *Trichoderma*.

Advantageous Effects

By using the method for converting to ginseng saponins according to the present invention, the desired ginseng saponin can be easily obtained with high yield.

BRIEF DESCRIPTION OF DRAWINGS

FIG. 1 shows the results of confirming compound K and compound Y produced after the conversion reaction of ginseng saponin though silica gel column chromatography.

DETAILED DESCRIPTION OF THE EMBODIMENTS

The present invention relates to a method for selectively producing compound K (chemical formula 1) and compound Y (chemical formula 2) from saponins of ginseng by an enzymatic method.

[Chemical Formula 1]

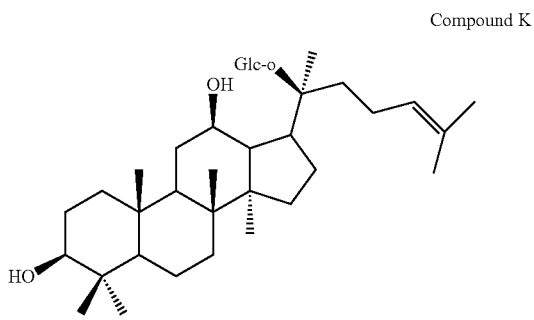

Compound K

[Chemical Formula 2]

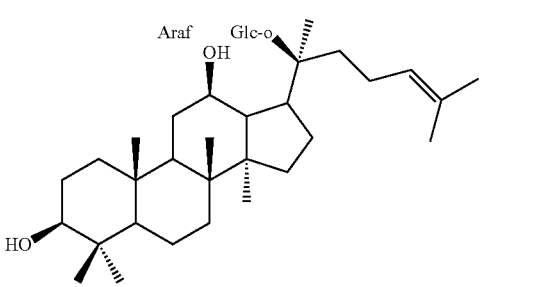

Compound Y

According to the method of the present invention, the conversion from saponin of ginseng, specifically panaxadiol-type saponin, more specifically ginsenosides Rb1, Rb2, Rc, Rd or a mixture thereof to a desired ginseng saponin can be efficiently carried out by using enzymes derived from microorganisms, thereby obtaining compound K and compound Y in high yield.

Specifically, the enzyme used in the present invention is obtained from a microorganisms belonging to the genus *Aspergillus* and a microorganism belonging to the genus *Trichoderma*, and the enzyme is preferably obtained from at least one microorganism of the genus *Aspergillus* selected from the group consisting of *Aspergillus niger*, *Aspergillus*

*aculeatus, Aspergillus luchuensis* and *Aspergillus oryzae*, and at least one microorganism of the genus *Trichoderma* selected from the group consisting of *Trichoderma aggressivum, Trichoderma harzianum, Trichoderma reesei* and *Trichoderma viride*, and those obtained from *Aspergillus aculeatus* and *Trichoderma reesei* are most preferred.

In addition, the enzyme used in the present invention may be naringinase, hemicellulase, beta-glucanase, lactase, cellulase, beta-galactosidase, or pectinase, isolated from the above microorganisms, and pectinase, naringinase, hemicellulase, or cellulase are preferred.

Even the same type of enzyme that performs mostly the same function, the site where the enzyme functions specifically in the substrate varies depending on the species of the microorganism from which the enzyme is derived, resulting in a difference in substrate specificity. Therefore, in the present invention, it is most preferable that at least one selected from the group consisting of pectinase, naringinase, cellulase and hemicellulase obtained from *Aspergillus aculeatus*; and at least one selected from the group consisting of pectinase, cellulase or a mixture thereof obtained from *Trichoderma reesei* are used at the same time.

In the present invention, saponin of ginseng is dissolved in a solvent in an amount of 0.01 to 20% by weight, and then the saponin is converted into the desired ginseng saponin by an enzymatic method using the above-mentioned enzyme. The solvents used here are preferably those that do not inhibit the activity of the enzyme, for example, an aqueous solvent such as water or a buffer solution, or a mixture of an aqueous solvent and an organic solvent such as water or a buffer solution can be used. Specifically, the buffer solution used here may be acetic acid, citric acid, phosphoric acid, citric acid-phosphoric acid, or the like, and the organic solvent may be acetonitrile, dioxane, dimethyl sulfoxide, methanol, ethanol, 1-propanol, 2-propanol, or the like. The pH range of the solvent that can be used is preferably 2.5 to 7.5, more preferably 3 to 6, still more preferably 3.5 to 5.5.

In the method of the present invention, the enzyme to be used is added in an amount of preferably 1 to 500% by weight, more preferably 10 to 400% by weight, still more preferably 10 to 200% by weight, based on the amount of the substrate used.

The reaction temperature must be a temperature condition under which no enzyme inactivation occur, but the temperature is maintained in the range of preferably 30 to 60° C., more preferably 35 to 60° C., still more preferably 40 to 55° C.

Furthermore, the reaction time is not particularly limited as long as it is a period during which the activity of the enzyme is maintained, but it is desirable to perform the reaction while stirring for 1 to 120 hours, preferably 1 to 96 hours, more preferably 24 to 96 hours, still more preferably 24 to 72 hours.

The enzymatic reaction can be carried out by adding two enzymes simultaneously, or in a sequential manner in which one enzyme is reacted first, and the remaining enzyme is subsequently added.

Subsequently, a reaction solution containing a large amount of compound K and compound Y can be obtained by inactivating the enzyme using a known method such as heating in a boiling water bath.

DETAILED DESCRIPTION OF THE EMBODIMENTS

Hereinafter, the present invention will be described in detail by way of Examples. However, these Examples are given for illustrative purposes only, and are not intended to limit the scope of the invention thereto.

Reference Example 1

Production of *Ginseng* Purified Saponin 20 l of ethanol was added to 2 kg of red ginseng, white ginseng, fresh ginseng, tiny-sized ginseng or leaves, flowers and fruits of ginseng, and extracted three times under reflux and then immersed at 15° C. for 6 days. Thereafter, the residue and the filtrate were isolated through filter cloth-filtration and centrifugation, and the isolated filtrate was concentrated under reduced pressure. The extract obtained was suspended in water, and then extracted five times with 1 l of ether to remove a pigment. The aqueous layer was extracted three times with 1 l of 1-butanol. The total 1-butanol layer thus obtained was treated with 5% KOH, washed with distilled water and then concentrated under reduced pressure to obtain 1-butanol extract, which was dissolved in a small amount of methanol, and then added to a large amount of ethyl acetate. The resulting precipitate was dried to thereby obtain 40 to 80 g of ginseng purified saponin (including ginsenoside Rb1, Rb2, Rc, Rd, Re, Rg1, Rf, etc.).

Example 1

Production of Compound K and Compound Y Through Enzymatic Reaction 10 g of ginseng purified saponin (including ginsenoside Rb1, Rb2, Rc, Rd, Re, Rg1, Rf, etc.) of the Reference Example 1 was dissolved in 1 l of water.

Thereafter, pectinase isolated from *Aspergillus aculeatus* and pectinase isolated from *Trichoderma reesei* were added to the above mixed solution at the same time. In this case, each of the above enzymes was added by 100% by weight relative to the substrate, and the mixture was reacted at 30° C. for 72 hours. When the substrate was completely disappeared by periodic confirmation by thin layer chromatography, the enzyme was inactivated by heating in a boiling water bath for 10 minutes, thereby completing the reaction. Finally, ethyl acetate was added to the reaction solution at a ratio of 1:1 (ratio of volume to the reaction solution), extracted three times, concentrated and then subjected to silica gel column chromatography (chloroform:methanol=9:1) to isolate compound K and compound Y (FIG. 1).

2.66 g of ginsenoside Rb1, 0.73 g of ginsenoside Rb2, 1.23 g of ginsenoside Rc and 0.38 g of ginsenoside Rd were present in 10 g of the ginseng saponin of Reference example 1 used. Compound K was converted from ginsenoside Rb1, ginsenoside Rc and ginsenoside Rd in a yield of 95% or more, and compound Y was converted from ginsenoside Rb2 in a yield of 95% or more.

The invention claimed is:
1. A method for producing compound K of the following Chemical Formula 1 and compound Y of the following Chemical Formula 2 from ginseng saponins comprising Rb1, Rb2, Rc and Rd, said method comprising converting the ginseng saponins to compound K and compound Y by contacting the ginseng saponins with enzymes, said enzymes comprising;
   a) pectinase obtained from *Aspergillus aculeatus*; and
   (b) pectinase obtained from *Trichoderma reesei*,
      to produce a reaction mixture comprising compound K and compound Y as conversion products:

Chemical Formula 1

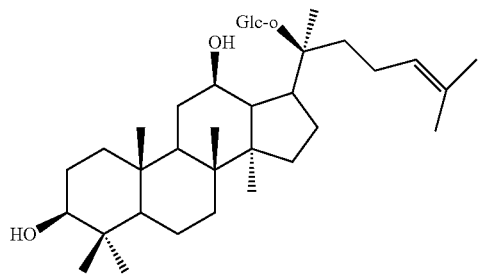

Chemical Formula 2

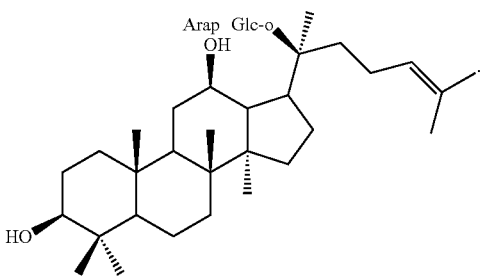

Compound K, where Glc is β-D-glucopyranosyl;
Compound Y, wherein Glc is β-D-glucopyranosyl and Arap is α-L-arabinopyranosyl.

2. The method according to claim 1, wherein the method comprises the steps of:

1) dissolving the ginseng saponins as a substrate in an aqueous solvent or a mixed solution of an aqueous solvent and an organic solvent, adding thereto the enzyme, and allowing the converting of the ginseng saponins by the enzyme to undergo thereby producing the reaction mixture comprising compound K and compound Y as conversion products;

2) inactivating the enzyme in the reaction mixture of 1) when the substrate of the reaction solution is completely disappeared, thereby completing the conversion reaction; and 3) adding ethyl acetate to the reaction mixture of 2), followed by extraction and concentration, thereby isolating compound K, and compound Y.

3. The method according to claim 2, wherein the (a) pectinase, obtained from the genus *Aspergillus aculeatus*; the (b) pectinase, obtained from the genus *Trichoderma reesei* are added simultaneously or sequentially.

4. The method according to claim 2, wherein the amount of the enzymes corresponds to 10 to 400% by weight based on the amount of the substrate.

5. The method according to claim 2, wherein the converting of 1) is carried out at a temperature of 35 to 60° C.

6. The method according to claim 2, wherein the converting of 1) is carried out for 24 to 96 hours.

7. The method according to claim 2, wherein the aqueous solvent or the mixed solution of an aqueous solvent and an organic solvent has a pH in the range of 3 to 6.

\* \* \* \* \*